US008192721B2

(12) United States Patent
Rowe

(10) Patent No.: US 8,192,721 B2
(45) Date of Patent: Jun. 5, 2012

(54) COMPOSITIONS USEFUL FOR REDUCING TOXICITY ASSOCIATED WITH GADOLINIUM-BASED CONTRAST AGENTS

(75) Inventor: Vernon D. Rowe, Shawnee, KS (US)

(73) Assignee: Verrow Pharmaceuticals, Inc., Lenexa, KS (US)

( * ) Notice: Subject to any disclaimer, the term of this patent is extended or adjusted under 35 U.S.C. 154(b) by 596 days.

(21) Appl. No.: 12/333,168

(22) Filed: Dec. 11, 2008

(65) Prior Publication Data

US 2009/0155181 A1    Jun. 18, 2009

Related U.S. Application Data

(60) Provisional application No. 61/013,456, filed on Dec. 13, 2007.

(51) Int. Cl.
*A61B 5/055* (2006.01)
(52) U.S. Cl. ............... 424/9.32; 424/9.3; 424/9.322
(58) Field of Classification Search ............... 424/9.3, 424/9.32, 9.322
See application file for complete search history.

(56) References Cited

U.S. PATENT DOCUMENTS

| | | | |
|---|---|---|---|
| 2,923,704 | A | 2/1960 | Berger et al. |
| 3,426,011 | A | 2/1969 | Parmerter et al. |
| 4,020,160 | A | 4/1977 | Bernstein et al. |
| 4,247,535 | A | 1/1981 | Lewis et al. |
| 4,258,180 | A | 3/1981 | Lewis et al. |
| 4,596,795 | A | 6/1986 | Pitha |
| 4,727,064 | A | 2/1988 | Pitha |
| 5,021,236 | A | 6/1991 | Gries et al. |
| 5,134,127 | A | 7/1992 | Stella et al. |
| 5,376,645 | A | 12/1994 | Stella et al. |
| 5,560,903 | A | 10/1996 | Gries et al. |
| 5,733,528 | A | 3/1998 | Felder et al. |
| 6,060,597 | A | 5/2000 | Tobe et al. |
| 6,165,995 | A | 12/2000 | Hilgers |
| 6,232,304 | B1 | 5/2001 | Kim et al. |
| 6,632,803 | B1 | 10/2003 | Hardin |
| 7,385,041 | B2 | 6/2008 | Chang et al. |
| 2006/0093554 | A1 * | 5/2006 | Platzek et al. ............... 424/1.69 |
| 2007/0123478 | A1 | 5/2007 | Rowe |
| 2007/0270380 | A1 | 11/2007 | Rowe |

FOREIGN PATENT DOCUMENTS

WO    WO 03/053475 A1  *  7/2003

OTHER PUBLICATIONS

Thompson, D. Chaubai, M.V. (2002) Cyclodextrins (CDS)—Excipients by Definition, Drug Delivery Systems by Function (Part I: Injectable Applications). Drug Delivery Technology, vol. 2, No. 7, p. 34, 36 and 38.*
Aime, S., Botta, M., Frullano, L., Geninatti Crich, S., Giovenzana, G.B., Pagliarin, R., Palmisano, G., Sisti, M. (1999) Contrast Agents for Magnetic Resonance Imaging: A Novel Route to Enhanced Relaxivities Based on the Interaction of a GdIII Chelate with Poly-beta-cyclodextrins. Chemistry: a European Journal, vol. 5, No. 4, p. 1253-1260.*
Singer, R.M. [online] [Retrieved on Oct. 26, 2011] A Review of Gadolinium-Based Contrast Agents in Magnetic Resonance Imaging. Retrieved from the internet <http://www.cewebsource.com/coursePDFs/ReviewGBCAsMRI.pdf>.*
Bailey et al. (2007) "A pilot study to investigate the effect of a hydration regime upon immediate and 24 h delayed MRI contrast agent reactions." Radiography 13 Suppl. 1: e90-e98.
Briguori et al. (2006) "Gadolinium-based contrast agents and nephrotoxicity in patients undergoing coronary artery procedures." Catheter Cardiovasc. Interv. 67: 175-80.
Captisol® Material Safety Data Sheet, Cydex, Inc. Mar. 15, 2004.
Cavasol® Material Safety Data Sheet, Wacker Chemie AG, Oct. 17, 2007.
Croft et al. (1983) "Synthesis of Chemically Modified Cyclodextrins" Tetrahedron 39(9):1417-1474.
D'Haese and De Broe (1994) "Gadolinium." in Handbook on Metals in Clinical and Analytical Chemistry. Seiler, et al., Eds., Marcel Dekker, Inc, New York, pp. 365-369.
FDA News P07-90, May 23, 2007, "FDA Requests Boxed Warning for Contrast Agents Used to Improve MRI Images."
Grobner et al. (2007) "Gadolinium and nephrogenic systemic fibrosis." Kidney Int. 72: 260-264.
Grobner (2006) "Gadolinium-a specific trigger for the development of nephrogenic fibrosing dermopathy and nephrogenic systemic fibrosis?" Nephrol. Dial. Transplant 21:1104-1108.
Harborg et al. (1995) "Assay of the active ingredient of an MRI contrast agent using Mid and Near infrared spectroscopy and multivariate calibration" J. Molecul. Structure 348: 139-142.
Magnevist®(brand of gadopentetate dimeglumine) Injection Prescribing Information, Bayer Healthcare Pharmaceuticals Inc. Revised Jun. 2007.
Marckmann et al. (2006) "Nephrogenic Systemic Fibrosis: Suspected Causative Role of Gadodiamide Used for Contrast-Enhanced Magnetic Resonance Imaging" J. Am. Soc. Nephrol., 17, 2359-2362.
Markmann et al. (2007) "Case-control study of gadodiamide-related nephrogenic systemic fibrosis" Nephrol. Dial. Transplant. 22: 3174-3178.
MultiHance®, (gadobenate dimeglumine) Injection Prescribing Information, Bracco Diagnostics, Inc., Revised May 2007.
Nortier et al. (2007) "Nephrogenic systemic fibrosis-the need for a multidisciplinary approach." Nephrol. Dial. Transplant 22: 3097-3101.
Omniscan™ (gadodiamide) Injection Prescribing Information, GE Healthcare, Revised Jun. 2007.
OptiMARK™ (gadoversetamide injection) Prescribing Information, Mallinkrodt Inc., Oct. 2008.
Othersen et al. (2007) "Nephrogenic systemic fibrosis after exposure to gadolinium in patients with renal failure." Nephrol Dial Transplant 22: 3179-3185.
Perazella (2007) "Nephrogenic systemic fibrosis, kidney disease, and gadolinium: is there a link?" Clin. J. Am Soc. Nephrol. 2: 200-202.
ProHance® Multipack™ (Gadoteridol) Injection Prescribing Information, Bracco Diagnostics, Inc. Revised Apr. 2006.
Remington's Pharmaceutical Sciences, 18th Ed. Gennaro Ed., 1990, Mack Publishing Co., Ch. 84, Parenteral Preparations, pp. 1545-1569.

(Continued)

*Primary Examiner* — Scarlett Goon
(74) *Attorney, Agent, or Firm* — Akerman Senterfitt

(57) ABSTRACT

The invention relates to compositions comprising a gadolinium-based contrast agent and a derivatized cyclodextrin. Further provided are methods for reducing the toxicity associated with gadolinium-based contrast agents.

12 Claims, 2 Drawing Sheets

OTHER PUBLICATIONS

Sotthivirat et al. (2007) "Evaluation of various properties of alternative salt forms of sulfobutylether-β-cyclodextrin, (SBE)$_{7M}$β-CD" Int. J. Phann. 330(1-2): 73-81.

Swan et al. (1999) "Safety and phannacokinetic profile of gadobenate dimeglumine in subjects with renal impairment." Invest Radiol 34: 443-448.

Test Catalog for the Mayo Clinic Mayo Medical Laboratories, Unit Code 89301, Retrieved Jan. 12, 2009.

Tweedle et al. (1995) "Biodistribution of Radiolabeled, Formulated Gadopentetate, Gadoteridol, Gadoterate, and Gadodiamide in Mice and Rats" Invest. Radiol. 30(6): 372-380.

* cited by examiner

COMPOSITIONS USEFUL FOR REDUCING TOXICITY ASSOCIATED WITH GADOLINIUM-BASED CONTRAST AGENTS

CROSS-REFERENCES TO RELATED APPLICATIONS

This application claims the benefit of U.S. provisional application No. 61/013,456, filed Dec. 13, 2007, the contents of which are incorporated herein by reference.

BACKGROUND OF THE INVENTION

Gadolinium-based contrast agents are commonly used to improve visibility of internal structures when a patient undergoes magnetic resonance imaging (MRI). These agents are typically administered intravenously immediately prior to imaging. Many contrast agents used in MRI cause toxicity in various areas of the body if they are not excreted rapidly by the kidney. These include for example, chelated organic gadolinium compounds which are not nephrotoxic in themselves, but which if retained in the body for extended periods of time release gadolinium ions which are toxic to various organs and cells of the body including skin, nerves, etc. The problems particularly occur in patients who are at risk for reduced kidney function. Serious diseases including nephrogenic systemic fibrosis (NSF) are among the consequences of this problem. (see, for example, Briguori et al., Catheter Cardiovasc. Intery (2006) 67(2): 175-80; Grobner et al., Kidney Int. (2007) 72(3): 260-4; Nortier et al., Nephrol. Dial. Transplant (2007) 22(11): 3097-101).

The FDA requested a boxed warning for contrast agents used to improve MRI images on May 23, 2007 stating that patients with severe kidney insufficiency who receive gadolinium-based agents are at risk for developing NSF, a debilitating and potentially fatal disease. In addition, patients just before or just after liver transplantation, or those with chronic liver disease, are also at risk for developing NSF if they are experiencing kidney insufficiency of any severity. The boxed warning is now included in each of the five gadolinium-based contrast agents currently approved for use in the United States. Thus, a need exists to reduce the toxicity that is caused by contrast agents in patients with risk factors for compromised renal function.

BRIEF SUMMARY OF THE INVENTION

The present invention provides compositions and methods to reduce toxicities caused by gadolinium-based contrast agents used in MRI in patients, particularly due to reduced renal excretion of these agents. The invention provides compositions comprising a gadolinium-based contrast agent, a derivatized cyclodextrin, and optionally a pharmaceutically acceptable carrier or diluent, where the molar ratio of the contrast agent to the cyclodextrin is greater than 1:1.

In one embodiment, the disclosure provides a composition comprising a gadolinium-based contrast agent and a derivatized cyclodextrin wherein the molar ratio of the contrast agent to the cyclodextrin is greater than 1:1; and wherein the cyclodextrin is of the formula:

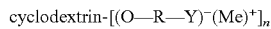

where R is selected from the group consisting of straight-chained or branched $C_{1-10}$ alkyl, alkenyl or alkynyl; $C_{3-8}$ cycloalkyl and $C_{3-8}$ aryl, each ring optionally containing 1 or more heteroatoms selected from S, N and O; and optionally substituted with halo or hydroxyl; Y is an anionic group selected from the group consisting of COO, $SO_4$, $SO_3$, $PO_3H$ and $PO_4$; Me is a pharmaceutically acceptable cation; and n is a number greater than or equal to 1. In one aspect, the composition further comprises a pharmaceutically acceptable carrier or diluent. The derivatized cyclodextrin is an alpha-, beta-, or gamma-cyclodextrin. In one aspect, the gadolinium-based contrast agent is selected from the group consisting of Gadodiamide; Gadoversetamide; Gadopentetate dimeglumine; Gadobenate dimeglumine; Gadoteridol; Gadoxetic acid disodium salt; Gadofosveset trisodium; Gadobutrol; and Gadoterate meglumine.

In one embodiment, the derivatized cyclodextrin is present in an amount effective for substantially inhibiting or ameliorating the toxic effect of the gadolinium-based contrast agent. In a specific aspect, R is $C_{1-10}$ alkyl and Y is $SO_3$, such that the derivatized cyclodextrin is a sulfoalkyl ether cyclodextrin.

In one embodiment, the molar ratio of the gadolinium-based contrast agent and the sulfoalkyl ether cyclodextrin in the composition is from about 1.1:1 to about 50:1; specifically from about 1.5:1 to about 50:1; and more specifically from about 2:1 to about 10:1.

In another embodiment, the disclosure provides a composition comprising a gadolinium-based contrast agent and a derivatized cyclodextrin wherein the molar ratio of the contrast agent to the cyclodextrin is greater than 1:1; and wherein the cyclodextrin is of the formula:

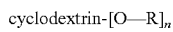

where R is selected from the group consisting of straight-chained or branched $C_{1-10}$ alkyl, alkenyl or alkynyl; $C_{3-8}$ cycloalkyl and $C_{3-8}$ aryl, each ring optionally containing 1 or more heteroatoms selected from S, N and O; and R is substituted with one or more hydroxyl groups; and n is a number greater than or equal to 1. The composition optionally comprises a pharmaceutically acceptable carrier or diluent. In one aspect, the gadolinium-based contrast agent is selected from the group consisting of Gadodiamide; Gadoversetamide; Gadopentetate dimeglumine; Gadobenate dimeglumine; Gadoteridol; Gadoxetic acid disodium salt; Gadofosveset trisodium; Gadobutrol; and Gadoterate meglumine.

In one embodiment, the derivatized cyclodextrin is present in an amount effective for substantially inhibiting or ameliorating the toxic effect of the gadolinium-based contrast agent. The composition comprises a cyclodextrin which is an alpha-, beta-, or gamma-cyclodextrin. In a specific aspect, R is $C_{1-10}$ alkyl, such that the derivatized cyclodextrin is a hydroxyalkyl cyclodextrin.

In one embodiment, the molar ratio of the gadolinium-based contrast agent and the hydroxyalkyl cyclodextrin in the composition is from about 1.1:1 to about 50:1; specifically from about 1.5:1 to about 50:1; and more specifically from about 2:1 to about 10:1.

The disclosure further provides a method of reducing the toxic effect of a gadolinium-based contrast agent comprising administering a composition of the disclosure to a subject. In certain specific aspects, the method of reducing the toxic effect of a gadolinium-based contrast agent comprises administering a composition comprising a gadolinium-based contrast agent and a derivatized cyclodextrin selected from sulfobutyl ether cyclodextrin, 2-hydroxypropyl cyclodextrin and 3-hydroxypropyl cyclodextrin.

The disclosure also provides a method of inhibiting or reducing toxicity associated with a gadolinium-based contrast agent, the method comprising concurrently administering to a subject a pharmaceutical composition comprising a gadolinium-based contrast agent and a pharmaceutical composition comprising a derivatized cyclodextrin; wherein the administered molar amount of the contrast agent is greater than the administered molar amount of the cyclodextrin. In one embodiment of the method, the gadolinium-based contrast agent of the composition is selected from the group consisting of Gadodiamide; Gadoversetamide; Gadopentetate dimeglumine; Gadobenate dimeglumine; Gadoteridol; Gadoxetic acid disodium salt; Gadofosveset trisodium; Gadobutrol; and Gadoterate meglumine; and the derivatized cyclodextrin is selected from sulfobutyl ether cyclodextrin, 2-hydroxypropyl beta-cyclodextrin or 3-hydroxypropyl beta-cyclodextrin.

The disclosure further provides a kit comprising two separate containers wherein the first container holds a gadolinium-based contrast agent formulation for injection and the second container holds a derivatized cyclodextrin formulation for injection.

DETAILED DESCRIPTION OF THE INVENTION

Figure 1:
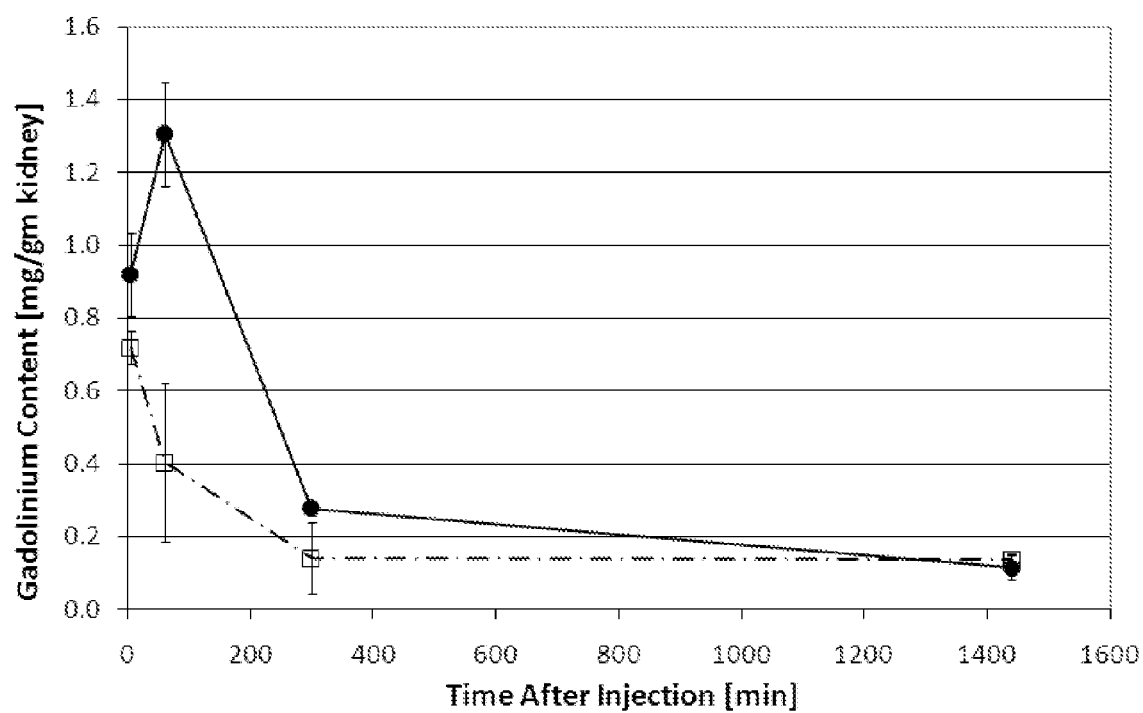
FIG. 1 shows the amounts of gadolinium appearing in the kidney of healthy mice at various times after intravenous dosing with gadopentate dimeglumine alone (□) or with gadopentate dimeglumine plus sulfobutyl ether β-cyclodextrin (●).

The present invention provides compositions and methods to reduce toxicities caused by gadolinium-based contrast agents used in MRI, including magnetic resonance angiography (MRA) in patients, particularly due to reduced renal excretion of these agents. The compositions of the present invention typically comprise a gadolinium-based contrast agent, a derivatized cyclodextrin, and optionally a pharmaceutically acceptable carrier, diluent or other excipient commonly used in the art. The derivatized cyclodextrin is present in an amount effective to substantially inhibit or ameliorate the toxic effect of the agent. In one embodiment, the derivatized cyclodextrin is a cyclodextrin having at least one anionic substituent selected from the group consisting of sulfonate, sulfate, carboxylate, phosphonate and phosphate. In one embodiment, the cyclodextrin has one or more anionic substituents selected from the group consisting of sulfonate and phosphate. In one embodiment, the derivatized cyclodextrin is a cyclodextrin sulfonate, preferably an α, β or γ-cyclodextrin sulfoalkyl ether. In a specific embodiment, the derivatized cyclodextrin is a sulfobutyl ether β-cyclodextrin having about 4 to about 8 sulfobutyl ether substituents per cyclodextrin molecule.

In another embodiment, the derivatized cyclodextrin has one or more neutral substituents. In one aspect, the neutral substituents are selected from the group consisting of straight chained or branched $C_{1-10}$ alkyl, preferably $C_{1-4}$ alkyl selected from methyl, ethyl, propyl and butyl, where each substituent is substituted with one or more hydroxyl groups. In a specific aspect, the cyclodextrin has at least one neutral substituent selected from the group consisting of 2-hydroxypropyl or 3-hydroxypropyl substituents.

The present invention also provides compositions having reduced toxic effect comprising an gadolinium-based contrast agent having toxic effects to tissues other than the kidney and a derivatized cyclodextrin. Toxic as used herein means toxic or destructive to one or more organs or tissues, or inducing disease states in an organ or tissue.

A "subject" as used herein, means a human or non-human mammal, including but not limited to, a dog, cat, horse, cow, pig, sheep, goat, chicken, primate, rat, and mouse.

The indefinite articles "a" and "an," as used herein in the specification and in the claims, unless clearly indicated to the contrary, should be understood to mean "at least one."

As used herein, "or" is understood to mean inclusively or, i.e., the inclusion of at least one, but including more than one, of a number or list of elements. Only terms clearly indicated to the contrary, such as "exclusively or" or "exactly one of," will refer to the inclusion of exactly one element of a number or list of elements.

MRI Contrast Agents

An MRI contrast agent may be any agent containing paramagnetic metal ions such as are used to enhance the visualization of internal organs, etc. These are agents useful for influencing the relaxation times in MRI diagnostics, contain at least one paramagnetic, physiologically compatible complex salt comprising a chelate from an open-chain or cyclic complex-forming compound containing organic nitrogen, phosphorus, oxygen and/or sulfur, and a complexed ion of the lanthanide elements of atomic number 57-70 or of the transition metals of atomic numbers 21-29, 42 and 44, and, optionally, an inorganic or organic base or acid, wherein said chelate complex is bound to a biomolecule. (see, for example, U.S. Pat. Nos. 5,021,236, 5,560,903, 5,733,528). Paramagnetic contrast agents include gadolinium (Gd)-based substances and agents containing manganese (Mn). Shortening of T1-relaxation time is the desired effect with the paramagnetic contrast agents, thereby increasing signal intensity (positive contrast enhancement). Gadolinium is a member of the lanthanide series of the periodic table of elements and is considered a nonessential element. Due to its paramagnetic properties, chelated gadolinium is commonly employed as contrast media for magnetic resonance imaging (MRI) and computer tomography (CT) scanning. (D'Hease and De Broe, Gadolinium. In Handbook on Metals in Clinical and Analytical Chemistry. Seiler, et al., Eds., Marcel Dekker, Inc, New York, 1994, pp 365-369).

The gadolinium contrast agents are used in MRI procedures. These extracellular fluid contrast agents are typically administered intravenously in a bolus dose, or by rapid venous infusion, immediately prior to imaging, and accumulate in lesions of abnormal vascularity in the brain and the body. Imaging is usually completed within about an hour following administration. The contrast agent serves to improve the resolution of MRI images by increasing the brightness in various parts of the body where the agent resides. Certain contrast agents may be used in magnetic resonance angiography (MRA) of, for example, the aorta, celiac artery, superior mesenteric artery, renal artery, and portal venous system.

In one embodiment, the MRI contrast agent is a gadolinium-based contrast agent. The paramagnetic gadolinium is chelated with various linear or cyclic molecules. Gadolinium based contrast agents include Gadodiamide (Omniscan™, GE Healthcare); Gadoversetamide (OptiMARK™, Mallinkrodt); Gadopentetate Dimeglumine (Magnevist®, Bayer Healthcare); Gadobenate Dimeglumine (MultiHance®, Bracco); Gadoteridol (ProHance®, Bracco); Gadoxetic acid disodium salt (Primovist®; Eovist®, Bayer Healthcare Pharmaceutical, Gd-EOB-DTPA); Gadofosveset trisodium (Vasovist®, EPIX Pharmaceuticals); Gadobutrol (Gadovist®, Schering, Germany); Gadoterate meglumine (Dotarem®, Guerbet, France). Five of the gadolinium-based MRI contrast agents, Gadodiamide, Gadoversetamide, Gadopentetate Dimeglumine, Gadobenate Dimeglumine, and Gadoteridol have been approved by the Food and Drug Administration (FDA) for use in the U.S. Eight contrast agents are approved for use in Europe. Each of the contrast agents is for administration by intravenous injection. Standard doses are generally about 0.0125 up to about 0.3 mmol/kg of body weight.

In one aspect, the contrast agent is Gadodiamide (Omniscan™, GE Healthcare) which is a formulation of the gadolinium complex of diethylenetriamine pentaacetic acid bismethylamide (Gd-DTPA-BMA) with a molecular weight (M.W.) of 573.66 g/mol with a formula $C_{16}H_{26}GdN_5O_8$.

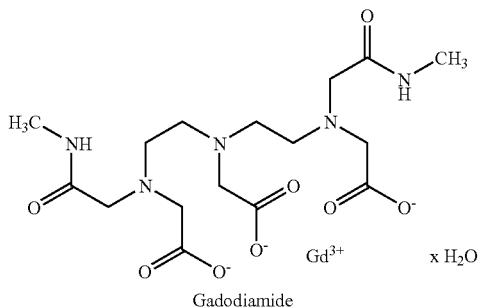
Gadodiamide

Gadodiamide is an injectable, nonionic extracellular enhancing agent for MRI. Gadodiamide is indicated for intravenous use in diagnostic magnetic resonance imaging to visualize lesions with abnormal vascularity in the brain, spine and associated tissues; and facilitate visualization of lesions with abnormal vascularity within the thoracic, abdominal, pelvic cavities and the retroperitoneal space. The recommended dosage of Gadodiamide is 0.05 to 0.1 mmol/kg.

In another aspect, the contrast agent is Gadoversetamide (OptiMARK™, Mallinkrodt) which is a formulation of a non-ionic gadolinium chelate of diethylenetriamine pentaacetic acid bismethoxyethylamide (Gd-DTPA-BMEA) with a M.W. of 661.77 g/mol with molecular formula $C_{20}H_{34}GdN_5O_{10}$.

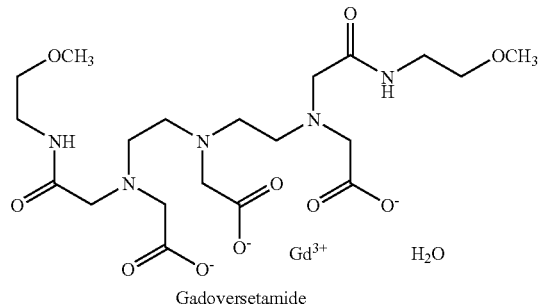
Gadoversetamide

Gadoversetamide is a linear nonionic agent. Gadoversetamide does not cross the blood brain barrier and is indicated for MRI imaging in patients with abnormal blood brain barrier or abnormal vascularity of the brain, spine and associated tissues and for contrast enhancement of liver lesions with abnormal vascularity. The recommended dosage of Gadoversetamide is 0.1 mmol/kg.

In a further aspect, the contrast agent is Gadopentetate Dimeglumine (Magnevist®, Schering, Germany) which is the N-methyl-glucamine salt of the gadolinium complex of diethylenetriamine pentaacetic acid (Gd-DTPA); 1-deoxy-1-(methylamino)-D-glucitol dihydrogen [N,N-bis[2-[bis(carbomethyl)amino]ethyl]-glycinato-(5'-)-]gadolinite (2-) (2:1), with molecular weight of 938 g/mol and a molecular formula $C_{14}H_{20}GdN_3O_{10}.2C_7H_{17}O_5$.

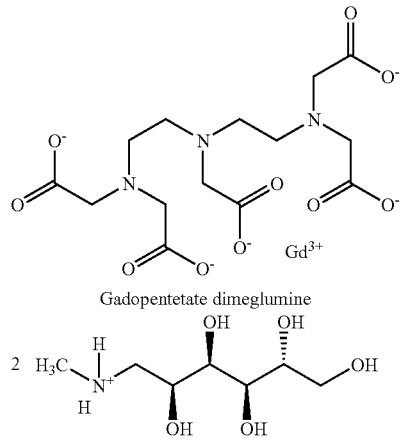
Gadopentetate dimeglumine

Gadopentetate dimeglumine is a linear, ionic contrast agent. Gadopentetate dimeglumine is indicated for MRI to visualize lesions with abnormal vascularity in the brain, spine, and associated tissues; and to facilitate visualization of lesions with abnormal vascularity in the head and neck; and in the body, excluding the heart. The recommended dosage Gadopentetate dimeglumine is 0.1 mmol/kg.

In one aspect, the contrast agent is Gadobenate dimeglumine (MultiHance®, Bracco, Italy). Gadobenate dimeglumine is a linear ionic contrast agent.

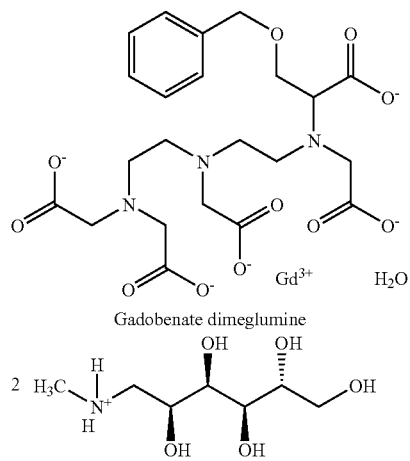
Gadobenate dimeglumine

Gadobenate dimeglumine is chemically designated as (4RS)-[4-carboxy-5,8,11-tris(carboxymethyl)-1-phenyl-2-oxa-5,8,11-triazatridecan-13-oato(5-)] gadolinate(2-) dihydrogen compound with 1-deoxy-2-(methylamino)-D-glucitol (1:2) with a molecular weight of 1058.2 and an empirical formula of $C_{22}H_{28}GdN_3O_{11}.2C_7H_{17}NO_5$. MultiHance® is indicated for intravenous use in magnetic resonance imaging (MRI) of the CNS in adults to visualize lesions with abnormal blood brain barrier or abnormal vascularity of the brain, spine, and associated tissues. The recommended dose of Gadobenate dimeglumine is 0.1 mmol/kg (0.2 mL/kg) administered as a rapid bolus intravenous injection.

In another aspect, the contrast agent is Gadoteridol (ProHance®, Bracco, Italy) which is the gadolinium complex of 10-(2-hydroxy-propyl)-1,4,7,10-tetraazacyclododecane-1,4,7-triacetic acid with a molecular weight of 558.7 g/mol, an empirical formula of $C_{17}H_{29}N_4O_7Gd$.

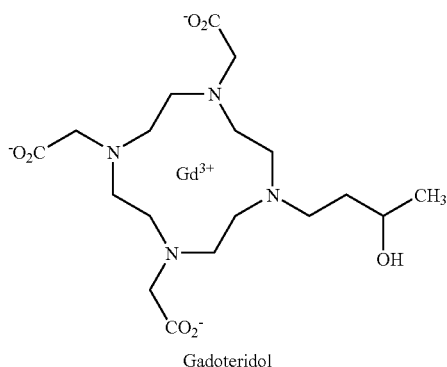

Gadoteridol

Gadoteridol is a cyclic nonionic contrast agent. ProHance® Injection is indicated for use in MRI in adults and children over 2 years of age to visualize lesions with abnormal vascularity in the brain (intracranial lesions), spine and associated tissues and for use in MRI in adults to visualize lesions in the head and neck. The recommended dose of ProHance® is 0.1 mmol/kg administered as a rapid intravenous infusion (10 mL/min-60 mL/min) or bolus (>60 mL/min). In patients suspected of having poorly enhancing lesions, in the presence of negative or equivocal scans, a second dose of 0.2 mmol/kg (0.4 mL/kg) may be given up to 30 minutes after the first dose.

In a further aspect, the contrast agent is Gadoxetic acid disodium salt (Primovist®, Bayer Healthcare Pharmaceutical, U.S.; gadoxetate disodium; Eovist®, Bayer Schering Pharma AG, Gd-EOB-DTPA).

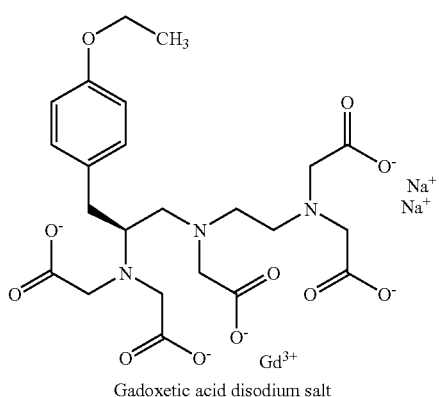

Gadoxetic acid disodium salt

Primovist® is a linear ionic contrast agent recently approve for use in the U.S. Gadoxetate is a complex between gadolinium ($Gd^{3+}$) and (4S)-4-ethoxybenzyl)-3,6,9-tris-(carboxylatomethyl)-3,6,9-triazaundecandoic acid (EOB-DTPA) with a molecular weight of 725.7142 g/mol and a molecular formula of $C_{23}H_{28}GdN_3O_{11} \cdot 2Na$. The structure of Gd-EOB-DTPA (Primovist®) has a similar complex core unit as that in Magnevist® "Gd-DTPA". However, Primovist® has a pendant ethoxybenzyl group covalently attached to the Gd-DTPA structure. The ethoxybenzyl group imparts greater lipophilicity to Primovist compared to that of Gd-DTPA complex in Magnevist®, resulting in weaker protein binding, which purportedly allows Gd-EOB-DTPA to enter the hepatocytes through membrane bound carriers. Primovist® is therefore liver specific and is indicated for imaging, detection and characterization of liver conditions including tumors, cysts and other malignant or benign lesions. The compound is taken up by the hepatocytes and brightens the signal of T1 weighted MR images immediately after contrast administration. The hepatocyte uptake will increase signal intensity from normal liver parenchyma. Lesions with no or minimal hepatocyte function, such as cysts, metastases, and most hepatic carcinomas, will remain unenhanced and are therefore more readily detected. The recommended dosage of Gadoxetic acid disodium salt is 12.5 to 25 umol/kg.

In one aspect, the contrast agent is Gadofosveset trisodium (Vasovist®, EPIX Pharmaceuticals; Bayer Schering AG) which is an injectable intravascular contrast agent designed to improve imaging of the vascular system using magnetic resonance angiography (MRA).

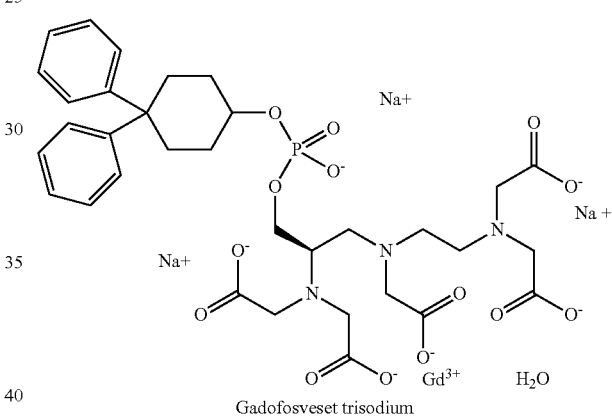

Gadofosveset trisodium

Gadofosveset trisodium, (Diphenylcyclohexyl phosphodiester-Gd-DTPA; N-(2-(bis(carboxymethyl)amino)ethyl)-N-((R)-2-(bis(carboxymethyl)amino)-3-hydroxypropyl)glycine 4,4-diphenylcyclohexyl hydrogen phosphate (6-)) gadolinate(3-), has a molecular formula of $C_{33}H_{38}GdN_3O_{14}P \cdot 3Na$ and molecular weight of 957.86 g/mol; the monohydrate has MW 975.879. Vasovist® reversibly binds to serum albumin, allowing imaging of the blood vessels for approximately an hour after administration. Vasovist® is indicated for contrast enhanced MRA visualization of abdominal or limb vessels in patients with suspected or known vascular disease. Vasovist® is currently marketed in Canada and several European countries. Phase III clinical trials are completed in the U.S. to determine efficacy in peripheral vascular disease and coronary artery disease. Recommended dosage is 0.03 mmol/kg.

In another aspect, the contrast agent is Gadobutrol (Gadovist®, Bayer, CA; Gd-DO3A-Butriol) which is a neutral complex consisting of gadolinium (Gd3+) and the macrocyclic compound dihydroxy-hydroxymethylpropyl-tetraazacyclododecane-triacetic acid (butrol). Therefore, gadobutrol is a cyclic, non-ionic contrast agent.

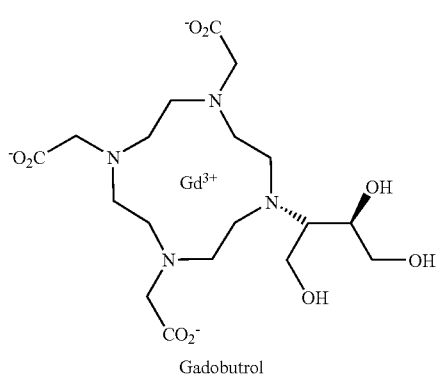

Gadobutrol

Gadobutrol, (10-((1RS,2SR)-2,3-Dihydroxy-1-(hydroxymethyl)propyl)-1,4,7,10-tetraazacyclododecane-1,4,7-triacetato(3-))gadolinium, has molecular formula $C_{18}H_{31}GdN_4O_9$ and molecular weight of 604.71 g/mol. Gadovist® is indicated for contrast enhancement during cranial and spinal MRI investigations and for contrast-enhanced magnetic resonance angiography (CE-MRA). Gadovist® is used for detection of very small lesions and for visualization of tumors that do not readily take up contrast media, for perfusion studies for the diagnosis of stroke, detection of focal cerebral ischemia and tumor perfusion. Recommended dosage is 0.1 to 0.3 mmol/kg body weight.

Gadoterate meglumine (Dotarem®, Gd-DOTA, Guerbet, France).

Gadoterate meglumine is a complex of gadopteric acid (Hydrogen (1,4,7,10-tetraazacyclododecane-1,4,7,10-tetraacetato(4))gadolinate(1-), $C_{16}H_{25}GdN_4O_8$, MW 558.64) and meglumine (1-Deoxy-1-(methylamino)-D-glucitol, $C_7H_{17}NO_5$, MW 195.21).

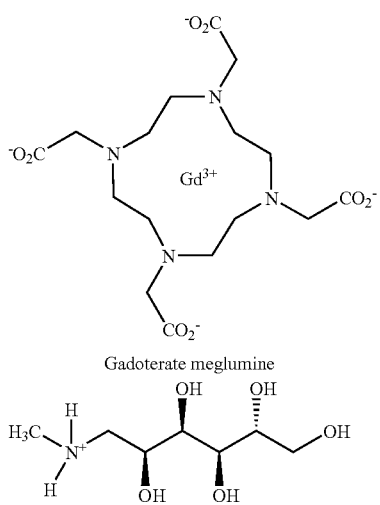

Gadoterate meglumine

Dotarem® is indicated for adults, children and infants for MRI for cerebral and medullary pathologies and other whole-body pathologies including angiography. Largely commercialized around the world since 1989, the approved indications for Dotarem® can vary between countries. Gadoterate meglumine is a cyclic, ionic contrast agent; therefore it is postulated to be one of the least likely of the currently used Gd3+ contrast agents to release free Gd3+ into the body. However, Dotarem® is not without toxicity and immediate and delayed adverse reactions include delayed headache, nausea, dizziness and problems with the injection site. (Bailey et al., 2007). Radiography 13 Suppl. 1: e90-e98. Recommended dosage is 0.1 to 0.2 mmol/kg body weight. A diluted from of Dotarem®, called Artirem®, is used as an arthrography-specific contrst agent for MRI. Artirim® is injected directly into the joints for visualization of particularly the ligament and tendon structures.

Gadolinium is eliminated primarily by the renal filtration. In healthy subjects with normal renal function, the plasma half-life of gadolinium is approximately 90 minutes. Patients with reduced renal function exhibit an increased gadolinium excretion half-life. (Swan et al., Safety and pharmacokinetic profile of gadobenate dimeglumine in subjects with renal impairment. Invest Radiol 1999; 34:443-448). Gadolinium has been associated with the nephrogenic systemic fibrosis (NSF) in patients with impaired renal function. (Otherson et al., Nephrogenic systemic fibrosis after exposure to gadolinium in patients with renal failure. Nephrol Dial Transplant 2007;10: 1093-1100).

Nephrogenic Systemic Fibrosis

Nephrogenic systemic fibrosis (NSF), originally named nephrogenic fibrosing dermopathy (NFD), was first recognized in 1997 in patients with renal insufficiency. NSF only occurs in patients with renal failure, acute or chronic, and particularly in patients with chronic kidney disease (CKD) stage 4 or 5 requiring dialysis.

A close association between development of NSF and exposure to gadolinium-containing contrast agents was first noted by Grobner (Nephrol. Dial. Transplant 2006; 21:1104-1108). This association was quickly confirmed by other groups. Marckmann et al. calculated an odds ratio of 32.5 to acquire NSF when exposed to gadodiamide. (Marckmann et al., J. Am. Soc. Nephrol. 2006, 17, 2359-2362.) These findings prompted the FDA to issue a public health advisory regarding gadolinium-containing contrast agents and a possible link to the development of NSF. Several official authorities (European Medicines Agency (EMEA), Pharmacovigilance Working Party (PhVWP), and the Committee on Medicinal Products for human use (CHMP) and the manufacturer of Gadodiamide (Omniscan™, Amersham Health, Oslo, Norway) have considered administration of gadodiamide to be contraindicated in patients with a glomerular filtration rate (GFR) less than 30 mL/min./1.73 $m^2$ and in liver transplant recipients. (Grobner et al., 2007).

In NSF, prolonged retention of gadolinium is thought to allow the gadolinium cation to dissociate from its synthetic organic chelator and deposit predominantly in the skin, although other organs may be affected as well. These patients are often severely debilitated by progressive skin thickening and tightening. Fibrosis of skeletal muscle, lungs, liver, testes, and myocardium have also been observed, often with fatal results. Because the ionic radius of gadolinium is similar to that of calcium (Swan et al., 1999), it may also deposit in bone. (D'Hease and De Broe., 1994). Clinically, NSF is characterized by initial swelling of distal parts of the extremities, cutaneous thickening, hardening or swelling and hyperpigmentation of the extremities or abdomen. Distinct nodules can be seen. Painful contractures of the joints may progressively result in reduced mobility. NSF may result in fatal or debilitating systemic fibrosis affecting the skin, muscle and internal organs.

According to the Test Catalog for the Mayo Clinic Mayo Medical Laboratories, Unit Code 89301, elevated gadolinium (>0.5 mcg/24-hour) observed in a 24 hour urine specimen collected more than 48 hours after administration of gadolinium-containing contrast media indicates impaired ability to eliminate gadolinium. These patients have an increased risk of developing NSF. Gadolinium in urine can be detected by inductively coupled plasma-mass spectrometry (ICP-MS). Three hemodialysis treatments are required to substantially remove gadolinium from patents with impaired renal function; peritoneal dialysis is not effective. (Perazella, Nephrogenic systemic fibrosis, kidney disease, and gadolinium: is there a link? Clin. J. AM Soc. Nephrol. 2007; 2: 200-202).

The mechanism by which some gadolinium containing contrast agents are more likely to trigger NSF than others have been related to their different physicochemical properties susceptible to affect the release of free Gd ions ($Gd^{3+}$). (Nortier et al., 2007). For example, the agents associated with the most cases of NSF, Omniscan™ and OptiMARK™, are non-ionic and are arranged in a linear structure theoretically facilitating the release of free $Gd^{3+}$ into the body by transmetallation with endogenous ions. However, Magnevist®, a linear ionic contrast agent, has also been associated with NSF cases. Nortier et al., 2007 reported that transmetallation is more likely to occur when $Gd^{3+}$ agents remain in the body for a long period as in the case of renal failure. Free $Gd^{3+}$ ions have been found deposited in tissues and organs from NSF patients.

Other Side Effects

In addition to NSF, other side effects of certain gadolinium-based contrast agents include acute renal failure requiring dialysis or worsening of renal function. Hypersensitivity reactions such as anaphylactoid and anaphylactic reactions with cardiovascular, respiratory and/or cutaneous manifestations can occur. More common adverse reactions of mild or moderate intensity include headache nausea, and dizziness.

Derivatized Cyclodextrins

Cyclodextrins (also referred to as "CD" or "CDs") are cyclic oligosaccharides consisting of at least six glucopyranose units. Although CDs with up to twelve glucopyranose units are known, only the first three homologs have been studied extensively, α, β, and γ, having 6, 7 and 8 glucopyranose units, respectively. For example, the β-cyclodextrin molecule is made up of seven α-1,4-linked glucopyranose units which form a cone-shaped molecule having a hydrophilic outer surface and a lipophilic cavity in the center. Cyclodextrins exist as conical shaped molecules with the primary hydroxyls situated at the small end of the cone and the secondary hydroxyls situated at the large opening to the cone.

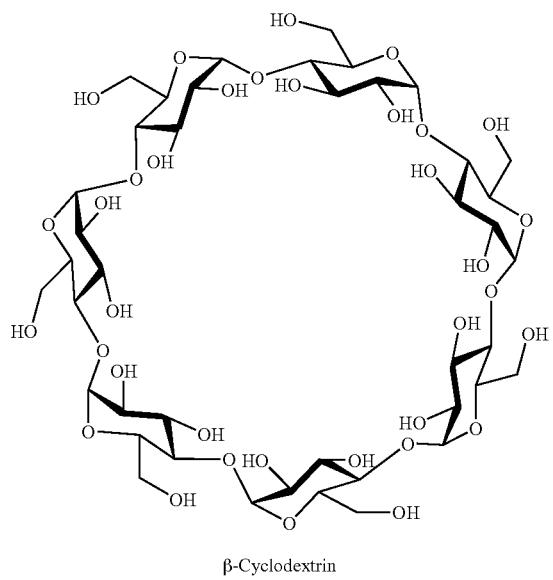

β-Cyclodextrin

Topographically, the CDs may be represented as a torus, the upper rim of which is lined with primary —CH$_2$OH groups, and the lower rim with secondary hydroxyl groups. Coaxially aligned with the torus is a channel-like cavity of about 5, 6 or 7.5 A.U. diameter for the α, β, and γ-CDs, respectively. These cavities make the cyclodextrins capable of forming inclusion compounds with hydrophobic guest molecules of suitable diameters.

A reasonably large number of CD derivatives have been prepared and described in the literature. In general, these chemically modified CDs are formed by reaction of the primary or secondary hydroxyl groups attached to carbons 2, 3 or 6 of the glucopyranose unit, without disturbing the α (1→4) hemiacetal linkages. A review of such preparations is given in Croft et al. (Synthesis of Chemically Modified Cyclodextrins, *Tetrahedron* (1983) 39(9):1417-1474), incorporated herein by reference.

In the derivatized cyclodextrins of the present invention, the primary, or secondary, hydroxyl groups of the cyclodextrin may be chemically derivatized. Modifications are generally made through substitution of the hydroxyl groups on the glucopyranose units, which would include up to 18 hydroxyl groups for α-CD; 21 for β-CD; and 24 for γ-CD.

In one embodiment, the derivatized cyclodextrins are of the formula:

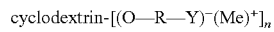

$$\text{cyclodextrin-}[(O\text{—}R\text{—}Y)^-(Me)^+]_n$$

where

R is selected from the group consisting of $C_{1-10}$ alkyl, alkenyl or alkynyl; $C_{3-8}$ cycloalkyl and $C_{3-8}$ aryl, each ring optionally containing 1 or more heteroatoms selected from S, N and O; and each of the aforementioned groups is optionally substituted with halo or hydroxyl; Y is an anionic group such as COO, SO$_3$, SO$_4$, PO$_3$H or PO$_4$; or a phosphorous, phosphinous, phosphonic, phosphinic, thiophosphonic, thiophosphinic and sulfonic acid;

Me is a pharmaceutically acceptable cation, such as lithium, sodium, potassium, calcium, magnesium, or aluminum, or an organic primary, secondary, or tertiary amine such as ammonium, methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like; and n is the number of substituents per oligosaccharide, each of which is independently selected, i.e., each substituent may be the same or different. For an individual cyclodextrin molecule, "n" will be a whole number greater than or equal to 1, the upper limit dependent upon the particular oligosaccharide.

In a population of oligosaccharides, it will be understood that n will represent the average number of substituents per saccharide molecule. As will be apparent to one of skill, n is 1 to 18 for α-CD; 1 to 21 for β-CD; and 1 to 24 for γ-CD. In the course of synthesis and use it is typical to have cyclodextrin derivatives that are a mixture of degrees of substitution. Thus derivatized cyclodextrins are sometimes quantified as having an average degree of substitution where n is an average value for the mixture and thus is not an integer.

According to one embodiment, R is $C_{1-10}$ alkyl, preferably $C_{1-4}$ alkyl selected from methyl, ethyl, propyl and butyl, each optionally substituted with halo or hydroxyl. Specifically preferred are oligosaccharides where in one or more groups, Y is SO$_3$.

It is generally preferred that the anionic-containing substituents be selected from the group consisting of sulfonate, sulfate, carboxylate, phosphonate and phosphate anionic groups and combinations thereof. The anionic substituents are preferably present in the molecule to an extent of from about 0.25 to about 3 substituents per sugar unit. Especially preferred compositions are those based on oligosaccharides having about 1 sulfonate substituent per sugar unit. Other preferred compositions are based on oligosaccharides having from about 2 to about 3 substituents per sugar unit, wherein the substituents comprise sulfate and/or phosphate substituents.

Anionic substituents include, by way of example, those described in U.S. Pat. No. 3,426,011, which is incorporated herein by reference. Preferably, the cyclodextrin will have at least one anionic substituent selected from the group consisting of sulfonate, sulfate, carboxylate, phosphonate and phosphate. According to one embodiment, R is straight chained or branched $C_{1-10}$ alkyl, preferably $C_{1-4}$ alkyl selected from methyl, ethyl, propyl and butyl, each optionally substituted with halo or hydroxyl.

Preferred CDs are sulfate derivatives of α, β, and γ-cyclodextrins. Preparation of cycloamylose sulfates and modified cyclodextrin sulfates are described in the art. See, for example, U.S. Pat. Nos. 2,923,704; 4,020,160; 4,247,535; 4,258,180; 4,596,795 and 4,727,064, each of which is hereby incorporated by reference. These cyclodextrin sulfates are typically associated with a physiologically acceptable cation.

Specifically preferred are derivatized cyclodextrins where in one or more groups, Y is $SO_3$. According to another embodiment, the hydroxyl groups are substituted with alkyl ether sulfonates of the formula —O—($C_1$-$C_8$ alkyl)-$SO_3$. In one preferred embodiment, commercially available Captisol® (β-cyclodextrin sulfobutyl ethers, SBE7-β-CD, Cydex Pharmaceuticals, Inc., Lenexa, Kans.) may be used, which is a sulfobutyl ether derivative of β-cyclodextrin in a sodium salt form having an average of seven sulfobutyl ether groups per cyclodextrin molecule (i.e., O—R—Y is —O—$(CH_2)_4$—$SO_3Na$). Captisol® does not exhibit the nephrotoxicity associated with underivatized β-cyclodextrin. In another aspect, alternative salt forms of sulfobutyl ether cyclodextrins are utilized such as, for example, potassium, calcium, and ethylene diamine salt forms as, for example, presented in Sotthivirat et al., Int. J. Pharm., 2007; 330(1-2):73-81.

In one embodiment, the derivatized cyclodextrins is of the formula:

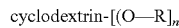

where R is selected from the group consisting of $C_{1-10}$ alkyl, alkenyl or alkynyl; $C_{3-8}$ cycloalkyl and $C_{3-8}$ aryl, each ring optionally containing 1 or more heteroatoms selected from S, N and O; and R is substituted with one or more hydroxyl groups; and n is the number of substituents per oligosaccharide, each of which is independently selected, i.e., each substituent may be the same or different. For an individual cyclodextrin molecule, "n" will be a whole number greater than or equal to one, the upper limit dependent upon the particular oligosaccharide. In a population of oligosaccharides, it will be understood that n will represent the average number of substituents per saccharide molecule.

According to one embodiment, R is $C_{1-10}$ alkyl, preferably $C_{1-4}$ alkyl selected from methyl, ethyl, propyl and butyl, each optionally substituted with halo or hydroxyl. Particularly preferred hydroxyl alkyl cyclodextrins include 2-hydroxypropyl β-cyclodextrin and 3-hydroxypropyl β-cyclodextrin.

Additional cyclodextrin derivatives are disclosed in U.S. Pat. Nos. 5,134,127; 5,376,645; 6,165,995 and 6,060,597, each of which is hereby incorporated by reference.

These derivatized cyclodextrins possess the ability to protect a patient from the toxicity associated with gadolinium-based contrast agents. Substituted cyclodextrins are preferred, at least in part, because of the relative uniformity and ease of production of such compounds, though other substitutions such as OH and other polar substituents may also be used.

Various vehicles, excipients, carriers and diluents can be utilized in the compositions of the disclosure. Certain parenteral formulations are described in, for example, Remington's Pharmaceutical Sciences, 18$^{th}$ Ed. Gennaro Ed., 1990, Mack Publishing Co., Ch. 84, Parenteral Preparations, pp 1545-1569. Aqueous vehicles, water-miscible vehicles, or non-aqueous vehicles may be employed. Typically, the formulations for intravenous injection are prepared in an aqueous vehicle, e.g. water for injection, and may optionally contain further excipients known in the art. Various solutes may be added for the purposes of enhancing solubility, patient comfort, chemical stability, and to preserve the preparation. Steps can be taken to remove or destroy pyrogens. Optional added substances can include buffers, antimicrobial agents, antioxidants, etc. Other excipients may include those excipients used in gadolinium based contrast agent formulations. These excipients include those which may serve to stabilize the gadolinium chelate such as various calcium excipients such as caldiamide sodium (Harborg et al., 1995, J. Molecul. Structure 348: 139-142), calcium hydroxide, calcium chloride dihydrate. (Tweedle et al., Invest. Radiol. 1995, 30(6): 372-380). Various calcium or zinc salts of the calcium of zinc salt of an organic ligand may be utilized such as those disclosed in U.S. Pat. No. 7,385,041, which is incorporated herein by reference. Excipients can also include meglumine, and trometamol (tromethamine). Various surfactants may optionally be employed, particularly for use with water-miscible vehicles, or non-aqueous vehicles. Sodium hydroxide and/or hydrochloric acid may be used to adjust the pH from about pH 5.5 to about pH 8.

Administration

The derivatized cyclodextrin may be complexed with the contrast agent, although it is not believed necessary for the protective effect of the composition. Although not bound by any theory regarding mechanism of action, it is believed that the derivatized cyclodextrin changes the tissue absorption of $Gd^{3+}$ and enhances excretion through the kidney. Thus, the amount of oligosaccharide is that amount which reduces the toxic effect of the agent.

Further provided are methods of reducing the toxic effect of a contrast agent comprising contacting the agent with a derivatized cyclodextrin. Methods are included for inhibiting or reducing toxicity associated with a contrast agent, comprising administering a pharmaceutical composition comprising a derivatized cyclodextrin, the agent and optionally a pharmaceutically acceptable carrier. Although it is preferred that administration occur as a single dose, the methods may also be effected by concurrently administering a pharmaceutical composition comprising a derivatized cyclodextrin and a pharmaceutical composition comprising the contrast agent, i.e., in separate doses. Where the agent and derivatized cyclodextrin are combined into a single dosage unit, they may be combined with a pharmaceutically acceptable carrier, or diluent, for example, a co-solution or dispersion in an inert pharmaceutically acceptable solvent or dispersing agent or the like.

Alternatively, the derivatized cyclodextrin can be separately formulated with pharmaceutically acceptable materials and administered separately; either concurrently with the agent or within about an hour before or after administration of the agent. By concurrently, it is meant administration of the separate doses occurs substantially at the same time such that both the derivatized cyclodextrin and the agent are present in vivo.

In one embodiment, the molar ratio of contrast agent:derivatized cyclodextrin is greater than 1:1, and may range from about 1.1:1 to about 50:1, preferably from about 1.5:1 to about 40:1; more preferably from about 2:1 to about 10:1. In the case of gadopentetate dimeglumine, by way of example only, it was found that a molar ratio of about 4:1 gadopentetate dimeglumine:Captisol® provided the desired effect of increasing urinary excretion of gadolinium.

The mode of administration, the dosage and frequency of dosage is governed by the mode of administration and dosage considerations conventionally employed with the contrast agent. Typically, these agents are administered by intravenous injection immediately prior to subjecting the patient to a magnetic resonance imaging procedure. The paramagnetic gadolinium ion alters the relaxation rates of the protons, enhancing the signal differentially in areas to which the gadolinium contrast agent has access. In patients with normal renal function, the agent (without derivatized cyclodextrin) is eliminated through the kidneys with half lives in the order of several minutes to a few hours. As mentioned above, it is believed that the compositions of the present invention facilitate the agents' excretion through the kidney with a reduced toxic side effect and increased safety profile.

Thus, for example, various combinations of the invention can be administered parenterally including, inter alia, intravenous, intra-arterial, intramuscular, subcutaneous, and intraperitoneal and joint injection. Preferably, the formulation is for parenteral administration, for example, intravenous administration. Other routes of administration may be utilized as dictated by medical and pharmacological practice related to the desired use of the particular contrast agent employed.

It will be understood that the specific dose level for any particular patient will depend upon a variety of factors including the specific agent employed, the age, body weight, general health, sex, diet, time of administration, route of administration and rate of excretion.

EXAMPLES

Example 1

Female C57BL/6 mice were injected intravenously with gadopentate dimeglumine either alone or combined with sulfobutylether β-cyclodextrin (SBEβCD). The mice were injected with 100 µl per 10 gram of body weight containing 5M gadopentate dimeglumine or 100 µl per 10 gram of body weight containing 5M gadopentate dimeglumine plus 0.125 M SBEβCD (mole ratio 1:0.025 Gd to SBEβCD). Mice (2 per time point) were sacrificed at times of 5 min, 60 min, 5 hr and 24 hrs post dosing. The kidneys were collected, but not perfused, and stored at −70° C. until analysis.

The content of gadolinium in the kidney samples was measured by ICPMS. Kidneys were digested (wet ashing) by incubation in concentrated nitric acid for 24 hrs followed by evaporation on a hot plate. The resultant residues were dissolved in high purity water.

The concentration of gadolinium in the kidneys as a function of time is presented in FIG. 1. The presence of the substituted cyclodextrin in the formulation resulted in a 1.9-fold enhancement in the AUC (area under the curve) indicating enhanced movement of gadolinium to and through the kidney.

Example 2

Female C57BL/6 mice were acclimated to metabolism cages and allowed ad lib food and water. The mice were made renal compromised by intraperitoneal injections of 10 mg/kg L-NAME (N-nitro-L-arginine methyl ester) followed by 10 mg/kg indomethacin 10 minutes later. Twenty minutes after the indomethacin dose, mice were injected intravenously with 1 µl/g body weight of either a solution of gadodiamide (0.5M, 287 mg/mL, Omniscan, GE Healthcare, Princeton, N.J.) or with a solution of gadodiamide plus dissolved sulfobutyl ether β-cyclodextrin (0.125 M, 270 mg/mL, Captisol®, CyDex Pharmaceuticals, Lenexa, Kans.). The mole ratio of gadolinium to cyclodextrin was 1:0.25, or 4:1). Urine was collected from each mouse throughout the study. At 24 hours post dosing, the animals were sacrificed and tissues were harvested and prepared for analysis. Blood was collected by direct cardiac puncture, the plasma was separated and stored at −70° C. until assay. Voided urine was collected, centrifuged, and immediately frozen on dry ice and stored at −70° C. until assay. Kidneys, liver and skin from the dorsum were collected on dry ice and stored at −70° C. until assay.

The content of gadolinium in the plasma, urine, kidney and skin samples was measured by ICP-MS. Urine samples were analyzed directly, while plasma samples were assayed following protein precipitated via the addition of acetonitrile (5 ul/ul of plasma). Kidneys were digested (wet ashing) by incubation in concentrated nitric acid for 24 hrs followed by evaporation on a hot plate. The resultant residues were dissolved in high purity water.

Figure 2:
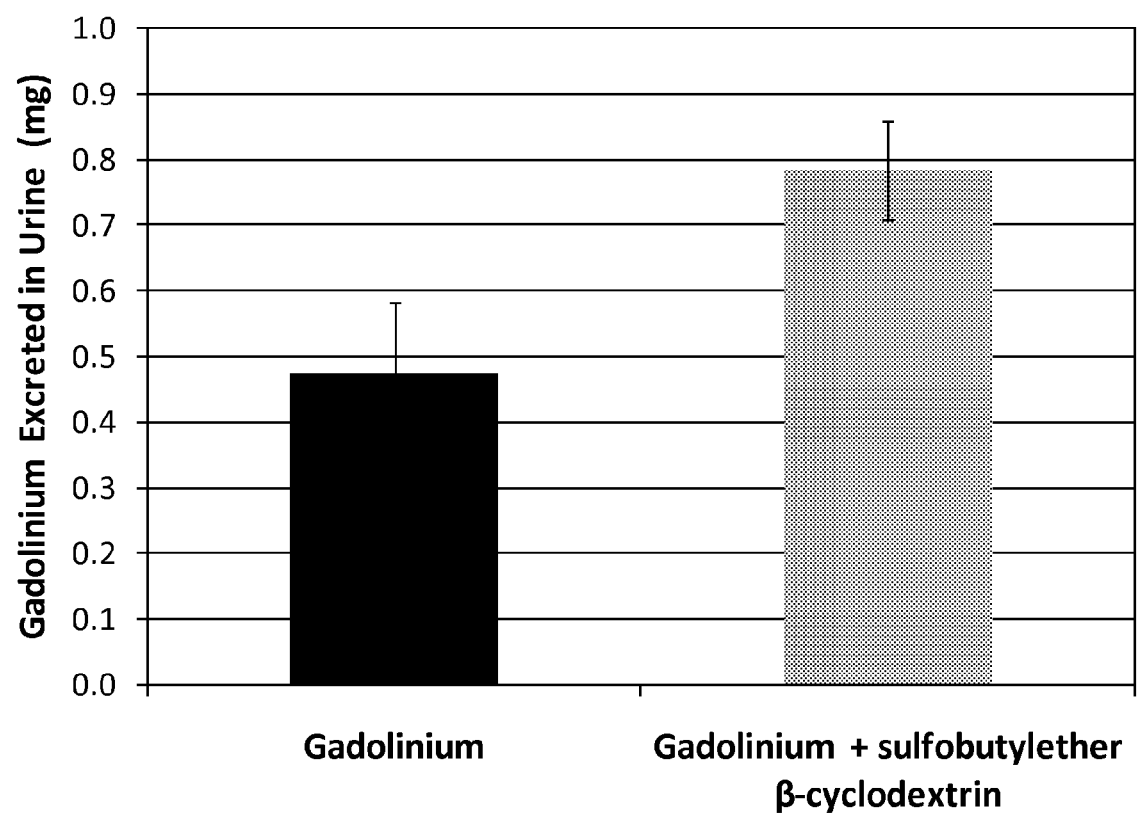
FIG. 2 shows amounts of gadolinium detected in the urine of renally compromised mice in the 24 hours following intravenous dosing with gadodiamide (n=6) or gadodiamide with a derivatized cyclodextrin (n=7).

Results for the excretion of gadolinium in the urine are presented in FIG. 2. The presence of the substituted cyclodextrin in the formulation resulted in a 1.7-fold enhancement in gadolinium elimination.

Example 3

An aqueous solution of gadodiamide is prepared. The formulation comprises 287 mg/mL gadodiamide (M.W. 573.66 g/mol), 270 mg/mL sulfobutyl ether beta-cyclodextrin (M.W. Captisol®, CyDex Pharmaceuticals, Lenexa, Kans., USA; if n=7, then M.W. 2242.07 g/mol) and 12 mg/mL caldiamide sodium in water for injection. The pH is adjusted with hydrochloric acid and/or sodium hydroxide to give a pH of 5.5 to 7.0. The solution is sterilized by filtration through a 0.22 micron pore size filter and aseptically filled into glass vials. The vials are sealed with a stopper and crimp cap.

Example 4

An aqueous solution of gadodiamide is prepared. The formulation comprises 287 mg/mL gadodiamide, 175 mg/mL 2-hydroxypropyl beta-cyclodextrin (Cavasol® W7 HP Pharma, Wacker Chemie AG., Adrian, Mich., USA) and 12 mg/mL caldiamide sodium in water for injection. The pH is adjusted with hydrochloric acid and/or sodium hydroxide to give a pH of 5.5 to 7.0. The solution is sterilized by filtration through a 0.22 micron pore size filter and aseptically filled into glass vials. The vials are sealed with a stopper and crimp cap.

Example 5

An aqueous solution of gadopentetate dimeglumine is prepared. The formulation comprises 469.01 mg/mL gadopentetate dimeglumine, 0.99 mg/mL meglumine, 0.40 mg/mL diethylenetriamine pentaacetic acid, and 168 mg/mL sulfobutyl ether alpha-cyclodextrin (degree of substitution ~4.5) in water for injection. The pH is adjusted with hydrochloric acid and/or sodium hydroxide to give a pH of 6.5 to 8.0. The solution is sterilized by filtration through a 0.22 micron pore size filter and aseptically filled into glass vials under a nitrogen headspace. The vials are sealed with a stopper and crimp cap.

I claim:

1. A composition comprising a gadolinium-based contrast agent and a derivatized cyclodextrin wherein
    the molar ratio of said agent to said cyclodextrin is from about 2:1 to 50:1;
    wherein the gadolinium-based contrast agent is selected from the group consisting of gadodiamide, gadoversetamide, gadopentetate dimeglumine, gadobenate dimeglumine, gadoteridol, gadoxetic acid disodium salt, gadofosveset trisodium, gadobutrol, and gadoterate meglumine; and
wherein
    said derivatized cyclodextrin is of the formula:

cyclodextrin-[(O—R—Y)⁻(Me)⁺]$_n$ where R is selected from the group consisting of straight-chained or branched $C_{1-10}$ alkyl, alkenyl or alkynyl; $C_{3-8}$ cycloalkyl and $C_{3-8}$ aryl, each ring optionally containing a heteroatom selected from S, N and O; and optionally substituted with halo or hydroxyl;
    Y is an anionic group selected from the group consisting of COO, $SO_4$, $SO_3$, $PO_3H$ and $PO_4$;
    Me is a pharmaceutically acceptable cation; and
    n is a number greater than or equal to 1; and
    wherein said derivatized cyclodextrin is present in an amount effective for inhibiting the toxic effect of said agent.

2. The composition of claim 1, wherein the composition consists essentially of the gadolinium-based contrast agent and the derivatized cyclodextrin.

3. The composition of claim 1 further comprising a pharmaceutically acceptable carrier or diluent.

4. The composition of claim 1 wherein said cyclodextrin of the formula cyclodextrin-[(O—R—Y)⁻(Me)⁺]$_n$ is an alpha-, beta-, or gamma-cyclodextrin.

5. The composition of claim 4 wherein R is $C_{1-10}$ alkyl and Y is $SO_3$, such that the derivatized cyclodextrin is a sulfoalkyl ether cyclodextrin.

6. The composition of claim 1 wherein the molar ratio of the gadolinium-based contrast agent to the sulfoalkyl ether cyclodextrin is from 2:1 to about 10:1.

7. The composition of claim 1 wherein the derivatized cyclodextrin is sulfobutyl ether beta-cyclodextrin and the cyclodextrin of the formula cyclodextrin-[(O—R—Y)⁻(Me)⁺]$_n$ is beta-cyclodextrin, O—R—Y)⁻ is O—$(CH_2)_4$—$SO_3$, Me is sodium, and n is about 7.

8. A composition comprising a gadolinium-based contrast agent and a derivatized cyclodextrin wherein,
    the gadolinium-based contrast agent is selected from the group consisting of gadodiamide, gadoversetamide, gadopentetate dimeglumine, gadobenate dimeglumine, gadoteridol, gadoxetic acid disodium salt, gadofosveset trisodium gadobutrol, and gadoterate meglumine;
    the molar ratio of said agent to said cyclodextrin is from about 2:1 to 50:1; and wherein
    said derivatized cyclodextrin is of the formula:

cyclodextrin-[O—R]$_n$ where R is selected from the group consisting of straight-chained or branched $C_{1-10}$ alkyl, alkenyl or alkynyl; $C_{3-8}$ cycloalkyl and $C_{3-8}$ aryl, each ring optionally containing a heteroatom selected from S, N and O; and R is substituted with one or more hydroxyl groups; and
    n is a number greater than or equal to 1; and
    wherein said derivatized cyclodextrin is present in an amount effective for inhibiting the toxic effect of said agent.

9. The composition of claim 8 further comprising a pharmaceutically acceptable carrier or diluent.

10. The composition of claim 8 wherein said cyclodextrin of the formula cyclodextrin-[O—R]$_n$ is an alpha-, beta-, or gamma-cyclodextrin.

11. The composition of claim 8 wherein R is $C_{1-10}$ alkyl, such that the derivatized cyclodextrin is a hydroxyalkyl cyclodextrin.

12. The composition of claim 11 wherein the molar ratio of the gadolinium-based contrast agent to the hydroxyalkyl cyclodextrin is from 2:1 to about 10:1.

* * * * *

UNITED STATES PATENT AND TRADEMARK OFFICE
CERTIFICATE OF CORRECTION

| | | |
|---|---|---|
| PATENT NO. | : 8,192,721 B2 | Page 1 of 1 |
| APPLICATION NO. | : 12/333168 | |
| DATED | : June 5, 2012 | |
| INVENTOR(S) | : Vernon D. Rowe | |

It is certified that error appears in the above-identified patent and that said Letters Patent is hereby corrected as shown below:

Column 17, line 14 in claim 1, remove the word "about"

Column 18, line 6 in claim 6, remove the word "about"

Column 18, line 20 in claim 8, remove the word "about"

Column 18, line 43 in claim 12, remove the word "about"

Signed and Sealed this
Fourteenth Day of August, 2012

David J. Kappos
*Director of the United States Patent and Trademark Office*